(12) United States Patent
Kobler et al.

(10) Patent No.: US 8,299,293 B2
(45) Date of Patent: Oct. 30, 2012

(54) PROCESS FOR PREPARING α-KETO ACIDS AND DERIVATIVES THEREOF

(75) Inventors: Christoph Kobler, Alzenau (DE); Martin Hateley, Munich (DE); Philipp Roth, Hanau (DE); Barbara Jaeger, Mainhausen (DE); Christoph Weckbecker, Gruendau-Lieblos (DE); Klaus Huthmacher, Gelnhausen (DE)

(73) Assignee: Evonik Degussa GmbH, Essen (DE)

( * ) Notice: Subject to any disclaimer, the term of this patent is extended or adjusted under 35 U.S.C. 154(b) by 723 days.

(21) Appl. No.: 12/169,683

(22) Filed: Jul. 9, 2008

(65) Prior Publication Data

US 2009/0076302 A1 Mar. 19, 2009

Related U.S. Application Data

(60) Provisional application No. 60/991,018, filed on Nov. 29, 2007.

(30) Foreign Application Priority Data

Jul. 9, 2007 (DE) .......................... 10 2007 031 917

(51) Int. Cl.
*C07C 323/22* (2006.01)
*C07C 69/66* (2006.01)
*C07C 67/36* (2006.01)
*C07C 69/73* (2006.01)
*C07C 59/00* (2006.01)

(52) U.S. Cl. ........ 560/152; 560/174; 560/175; 560/186; 562/577

(58) Field of Classification Search .......................... None
See application file for complete search history.

(56) References Cited

U.S. PATENT DOCUMENTS

| 5,627,185 A | 5/1997 | Gosselin et al. |
| 7,815,950 B2 | 10/2010 | Kobler et al. |
| 8,158,186 B2 | 4/2012 | Kobler et al. |
| 2009/0076302 A1 | 3/2009 | Kobler et al. |

FOREIGN PATENT DOCUMENTS

| WO | 96/33201 | 10/1996 |
| WO | WO 2006/072711 A1 | 7/2006 |

OTHER PUBLICATIONS

Carruthers, Some Modern Methods of Organic Synthesis, 2nd Edition, 1978, pp. 44-53.*
Greene, Protective Groups in Organic Chemistry, 1981, Jon Wiley & Sons, Inc., New York, pp. 129-132.*
Stacy et al, Journal of Organic Chemistry, Cortical Steroid Analogs. IV. Gem-Dialkylacetylcarbinols, Hydroxy Enol Ethers, and Hydroxy Ketals from the Reaction of Grignard Reagents and Ethyl Pyruvate Ketal 1966), 31(6), 1753-1757.*
B. M. Trost, et al., "Applications of Sulfenylations of Ester Enolates, Synthesis of Pheromones of the Honey Bee", XP 002504043, 1975, J. Org. Chem., vol. 40, No. 1, pp. 148-150.
A.I. Meyers, et al., "The Use of Dithioesters as Acyl Anion Equivalents. Double Homologation of the "$CH_2$-C=0" Synthon", XP 002504044, 1978, Tetrahedron Letters, No. 47, pp. 4657-4660.
Database: Beilstein, Beilstein Institute for Organic Chemistry, Database Accession No. BRN 1729347, XP 002504046, 1 Page.
Database: Beilstein, Beilstein Institute for Organic Chemistry, Database Accession No. BRN 2536576, XP 002504047, 2 Pages.
Database: Beilstein, Beilstein Institute for Organic Chemistry, Database Accession No. BRN 6393736, XP 002504048, 2 Pages.
Database: Beilstein, Beilstein Institute for Organic Chemistry, Database Accession No. BRN 1937904, XP 002504049, 1 Page.
Database: Beilstein, Beilstein Institute for Organic Chemistry, Database Accession No. BRN 1944840, XP 002504050, 2 Pages.
Database: Beilstein, Beilstein Institute for Organic Chemistry, Database Accession No. BRN 1937791, XP 002504051, 2 Pages.
Database: Beilstein, Beilstein Institute for Organic Chemistry, Database Accession No. BRN 1863371, XP 002504052. 1 Page.
Database: Beilstein, Beilstein Institute for Organic Chemistry, Database Accession No. BRN 5600320, XP 002504053, 2 Pages.
Database: Beilstein, Beilstein Institute for Organic Chemistry, Database Accession No. BRN 1772265, XP 002504054, 2 Pages.
R. J. Cregge, et al., "A Versatile and Reactive Michael Receptor for the Synthesis of 1,4-Dicarbonyl Compounds", XP 002504045, 1973, Tetrahedron Letters, No. 28, pp. 2603-2606.
Database: Beilstein, Beilstein Institute for Organic Chemistry, Database Accession No. Reaction 3780578, XP 002504055, 1 Page.
Database: Beilstein, Beilstein Institute for Organic Chemistry, Database Accession No. BRN 1765525, XP 002504056, 2 Pages.
Database: Beilstein, Beilstein Institute for Organic Chemistry, Database Accession No. Reaction 4688389, XP 002504057, 1 Page.
Driss Qasmi, et al., "Synthesis of N-Glyoxylyl Peptides and Their In Vitro Evaluation as HIV-1 Protease Inhibitors" XP 000889656, Jan. 1, 1997, Bioorganic & Medicinal Chemistry, vol. 5, No. 4, pp. 707-714.

* cited by examiner

*Primary Examiner* — Paul A Zucker
(74) *Attorney, Agent, or Firm* — Oblon, Spivak, McClelland, Maier & Neustadt, L.L.P.

(57) ABSTRACT

A method for preparing α-keto acids, especially α-ketomethionine, and/or derivatives thereof, whereby an aldehyde is reacted with thiols to give a corresponding dithioacetal, the dithioacetal formed, is reacted with an electrophile in the presence of a strong base, and the resulting α,α-(dithio)carboxylic acid is solvolyzed with acid-catalysis to release thiol and give the α-keto acid or a derivative thereof. Umpolung of aliphatic or aromatic aldehydes is effected by reaction with thiols.

20 Claims, No Drawings

PROCESS FOR PREPARING α-KETO ACIDS AND DERIVATIVES THEREOF

CROSS REFERENCE TO RELATED APPLICATIONS

This application claims priority to German Application No. 102007031917.9, filed Jul. 9, 2007, and U.S. Provisional Patent Application 60/991,018, filed Nov. 29, 2007, the disclosures of which are incorporated herein by reference in their entireties.

FIELD OF THE INVENTION

The present invention relates to a novel process for preparing α-keto acids, especially α-ketomethionine, and derivatives thereof.

BACKGROUND OF THE INVENTION

α-Keto acids have many uses including the supplementation of amino acids in the treatment of chronic kidney failure (Jungers et al., Blood Purification 1988, 6, 299-314 and Clasen et al., Med. Klin. 1978, 73, 1403-1408). Conventional methods for the synthesis of α-keto acids have been described in the literature. In one method a Grignard reagent is reacted with a dialkyl oxalate and subsequent hydrolysis of the resulting ester yields the free acid (Rambaud et al., Synthesis 1988, 564 and Macritchie et al., Tetrahedron: Asymmetry 1997, 8, 3895). The acid catalyzed hydrolysis of acyl cyanides affords α-keto acids (Nozaki et al., Tetrahedron: Asymmetry 1993, 4, 2179). Billek reports the preparation of a series of α-keto acids. In this preparation, alkylidene-hydantoins are hydrolyzed under basic reaction conditions (Billek, Monath. Chem. 1961, 92, 343-352).

α-Keto acids may be prepared from a corresponding aldehyde by an umpolung reaction. One means of subjecting the aldehyde to umpolung is the formation of a cyclic dithiane, from which a carbanion can be formed by deprotonation with a strong base. This carbanion can subsequently be reacted with carbon dioxide. The cyclic dithiane is finally split under oxidative conditions, for example with mercury salts, to give the desired α-keto acid.

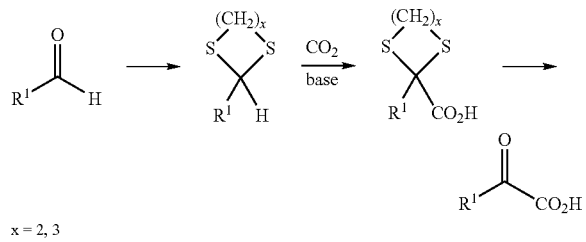

x = 2, 3

According to studies by Corey and Seebach [Corey et al., Angew. Chem. 1965, 77, 1134-1136 and Seebach et al., J. Org. Chem. 1975, 40, 231-237], dithiols are typically used in order to synthesize cyclic dithioacetals (dithianes). The formation of cyclic five or six membered ring dithianes proceeds preferentially as a result of kinetic preference for cyclization and the high thermodynamic stability of the five- or six-membered ring formed. This high stability, however, is a serious disadvantage, because chemically severe conditions are required to cleave the dithiane ring and release the desired α-keto acid. The cleavage of the dithiane is normally brought about by an oxidation process [Seebach, Synthesis 1969, 17-36]. In this oxidation, the sulfur of the dithiol component being removed is oxidized and then precipitated as a sparingly soluble mercury salt. Therefore, recycle and reuse of the dithiol is not possible. Further disadvantages of this process are the high costs of suitable dithiols, for example, 1,2-ethanedithiol or 1,3-propanedithiol, and the small amounts which would be available for industrial scale use. These problems make the industrial use of the above-described umpolung method very unattractive.

The reaction of short-chain thiols, for example, methyl mercaptan, with aldehydes to give the corresponding thioacetals [Trofimov et al., J. Org. Chem. USSR 1972, 8, 2036 and Rothstein et al., J. Chem. Soc. 1940, 1563] and the use of these dithioacetals in umpolung reactions with various electrophiles is described. However, there is only one literature example of umpolung where the electrophile is $CO_2$ and in that case the thioacetal is aromatic [Micetich et al., Heterocycles 1985, 23, 585-592].

α-Ketomethionine is an α-keto acid of great interest and utility, since it is formed as an intermediate in the organism in the course of conversion of D-methionine to L-methionine.

α-Ketomethionine and its derivatives, for example, its salts or esters, are particularly important compounds, since they constitute alternatives to methionine and to methionine hydroxy analog (MHA) as animal feed additives.

In 1942, Rudolph et al. reported that the sodium salt of α-ketomethionine can be used as a replacement for D,L-methionine, and that it accelerates the growth of young rats (Rudolph et al., J. Biol. Chem. 1942, 145, 210).

It has been shown several times that α-ketomethionine can provide the sulfur required for the biosynthesis of L-methionine and L-cysteine (Sizer et al., Poultry Sci. 1964, 44, 673; Baker et al., Poultry Sci. 1975, 54, 584 and Baker, J. Nutr. 1976, 106, 1376).

In addition, Baker and Harter were able to show that the calcium salt of α-ketomethionine has a relative biological value with regard to the growth of chickens of 83% compared to L-methionine (100%) and MHA (53%) (Baker and Harter, Proceedings of the Society for Experimental Biology and Medicine 1977, 156, 201). The relative biological value of various methionine derivatives, including α-ketomethionine (90% compared to L-methionine), was published by Baker in "Utilization of Precursors for L-Amino Acids" on page 39.

The use of α-ketomethionine and of its salts and esters and amides as an animal feed additive is described in WO 06-72711.

α-Ketomethionine, several salts and other derivatives, such as, for example, ketomethionine esters, are described in the literature. Conventional processes for preparing α-ketomethionine can be divided into chemical and biochemical processes:

a) Biochemical Syntheses:

Meister obtained the sodium salt of α-ketomethionine in a yield of 77% by the oxidation, catalyzed by L-aminooxidases, of methionine (Meister, J. Biol. Chem. 1952, 197, 309). Before that, Waelsch et al., showed that the aminooxidases present in the liver can convert methionine to α-ketomethionine (Waelsch et al., J. Am. Chem. Soc. 1938, 61, 2252).

Mosbach et al. likewise describe the preparation of α-ketomethionine by the oxidation, catalyzed by L-aminooxidases, of methionine. In this preparation, immobilized Providencia sp. PCM 1298 cells are used (Mosbach et al. Enzyme Microb. Technol. 1982, 4, 409).

The disadvantages of the preparation of α-ketomethionine or derivatives thereof with the aid of biological systems, either using purified enzymes or whole cells, are usually the relatively low space-time yields and the technically complicated isolation and product purification. An additional factor in the case of use of high-purity enzymes is that the development, production and purification of the enzymes is very expensive and complicated, and the reuse of already used enzymes is usually not possible.

b) Chemical Syntheses:

In 1957, Sakurai et al. published a first chemical synthesis route for preparing α-ketomethionine. As the key step, methyl α-methoxalyl-γ-methylmercaptopropionate was hydrolyzed with dilute hydrochloric acid to α-ketomethionine (Sakurai et al., J. Biochem. 1957, 44, 9, 557).

Almost at the same time, Yamada et al. published the same synthesis route after first attempts to prepare α-ketomethionine via an α-oximo ester which had been formed as an intermediate afforded only relatively low yields (Chibata et al., Bull. Agr. Chem. Soc. Japan 1957, 21, 336).

The process disclosed by Sakurai and Yamada has the disadvantage that considerable amounts of salt are formed, and therefore, implementation of this process on an industrial scale is not practical. In addition, the synthesis route is not atom-economic, since some of the molecule is eliminated as carbon dioxide in a synthesis step and is thus lost. An industrial scale implementation of this synthesis route would therefore be too expensive, inefficient and environmentally problematic.

Patent application WO 06-72711 describes preparation of α-ketomethionine proceeding from butadiene. In this preparation, butadiene is oxidized selectively to the unsaturated monoepoxide and then converted to the corresponding 1,2-diol by an acid-catalyzed ring opening with water. The subsequent oxidation of the 1,2-diol to the α,β-unsaturated α-keto acid and the subsequent 1,4 addition of MeSH leads to α-ketomethionine.

The high cost of butadiene renders this process unattractive as an industrial scale method to synthesize α-ketomethionine. It is probable that the price of butadiene will again rise significantly in the years to come depending on the price of crude oil. A further disadvantage of the process described in WO 06-727211 is the fact that existing conventional plants for methionine or MHA production could not be used, and therefore, new production plants for every individual process step described would have to be built. The synthesis route described in WO 06-72711 always leads to the free α-ketomethionine, which is unstable and very difficult to isolate.

DETAILED DESCRIPTION OF THE INVENTION

In view of the disadvantages of the described conventional methods of synthesis, the present invention seeks to provide a process for preparing α-keto acids, especially α-ketomethionine and its derivatives, in existing plants, in good yield, using low cost, readily available starting materials and without generating waste which is hazardous to the environment. Such α-keto acids, especially α-ketomethionine and its derivatives, may be useful as alternatives to methionine or MHA as animal feed additives.

The embodiments of the invention described herein achieve this objective.

The first embodiment of this invention provides a process for preparing α-keto acids and derivatives thereof of the general formula (I) or (II).

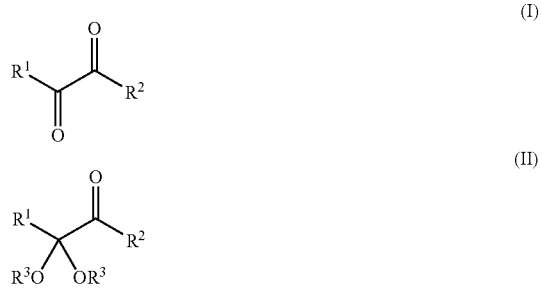

In general formulas (I) and (II):

$R^1$ is a branched or straight-chain $C_1$-$C_{18}$-alkyl, $C_5$-$C_8$-cycloalkyl, vinyl, allyl, $C_6$-$C_{10}$-aryl-$C_1$-$C_4$-alkylene, preferably benzyl, or $C_4$-$C_9$-heteroaryl-$C_1$-$C_4$-alkylene group, preferably 4-imidazolylmethylene or 3-indolylmethylene, where $R^1$ is optionally substituted by —SH, —SCH$_3$, —COOH, —CONH$_2$, —CHO, guanidyl, —OH, —NR'R" or —SS—CH$_2$—C(H)NH$_2$—CO$_2$H, where R' and R" are each as defined below;

$R^1$ is preferably vinyl or a branched or straight-chain, optionally substituted $C_1$-$C_8$-alkyl, preferably vinyl, or a branched or straight-chain, optionally substituted $C_1$-$C_4$-alkyl such as methyl, ethyl, n-propyl, i-propyl, n-butyl, sec-butyl and tert-butyl;

$R^1$ is most preferably vinyl, n-propyl or 2-(methylthio)ethyl, especially 2-(methylthio)ethyl;

$R^2$ is —OR''' or —NR'R", in which R' and R" may be the same or different and are each a hydrogen atom or a branched or straight-chain $C_1$-$C_6$-alkyl group, and R''' is a hydrogen atom, a branched or straight-chain $C_1$-$C_8$-alkyl, $C_5$-$C_8$-cycloalkyl, allyl or a benzyl group, where alkyl in R', R' and/or R''' is optionally substituted, or R''' is an alkaline metal ion, alkaline earth metal ion or a mono- or divalent transition metal ion;

$R^2$ is preferably —OR''', in which R''' is a hydrogen atom or a branched or straight-chain $C_1$-$C_4$-alkyl group;

$R^3$ is the same or different and is a hydrogen atom, a branched or straight-chain $C_1$-$C_8$-alkyl, allyl or a benzyl group, where alkyl and/or benzyl is optionally substituted, or the two $R^3$ radicals together are $C_2$-$C_8$-alkanediyl and together form a ring, or the two $R^3$ and R''' radicals together are part of a $C_3$-$C_8$-alkanetriyl group of the general formula —$R^3$(CH—)R''' and together form a bicyclic group;

$R^3$ is independently preferably a hydrogen atom or a branched or straight-chain, optionally substituted $C_1$-$C_4$-alkyl group, especially i-propyl or i-butyl, or the two $R^3$ radicals together are $C_2$-$C_4$-alkanediyl and together form a ring, or the two $R^3$ and R''' radicals together are part of a $C_3$-$C_6$-alkanetriyl group of the general formula —$R_3$(CH—)R''' and together form a bicyclic group.

The method for the preparation of α-keto acids of general formula (I) and derivatives of α-keto acids of the general formula (II) according to the claimed invention comprises:

a) reacting an aldehyde of the formula, $R^1$CHO, with at least two thiols of the formula $R^4$—S—H, to give a corresponding dithioacetal;

b) reacting the dithioacetal with a carbonyl-containing electrophile in the presence of a strong base and hydrolyzing in a solvent of general formula $R^5$OH to give an α,α-(dithio)carboxylic acid or derivatives thereof of formula (III):

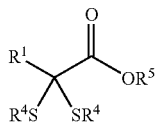

(III)

c) converting the α,α-(dithio)carboxylic acid or derivatives thereof of the formula (III) by acid-catalyzed solvolysis in the presence of at least 1 molar equivalent of water with release of thiols of the formula $R^4SH$ to give the α-keto acid of general formula (I) or derivatives of the general formula (II);

wherein $R^4$ is a branched or straight-chain, optionally substituted $C_1$-$C_6$-alkyl, $C_5$-$C_8$-cycloalkyl, allyl or benzyl group, preferably methyl or ethyl, especially methyl, and $R^5$ is a hydrogen atom or a branched or straight-chain $C_1$-$C_6$-alkyl group, and $R^1$ is as described above.

In the process according to the invention, a noncyclic dithioacetal may initially be formed (step a)).

The dithioacetal obtained in a) may then be converted by an umpolung reaction with a carbonyl-containing electrophile, for example, carbon dioxide, phosgene, chloroformic esters, orthoformic esters or dialkyl carbonate (step b)) in the presence of a base to an α,α-(dithio)carboxylic acid or derivatives thereof. The electrophile used may preferably be carbon dioxide, which can be used in the form of a gas, solid (e.g. dry ice) or liquid (in supercritical form or as a solvent).

For the deprotonation which is effected first in b), bases whose corresponding acid has a $pK_a$ value of >20 are particularly suitable. Preferred bases include alkyllithium compounds, especially n-butyllithium and tert-butyllithium, metal amides and hydrides, especially sodium amide and sodium hydride, and metal hydroxides or carbonates alone or in combination with chelating ligands, for example, crown ethers, preferably potassium hydroxide or potassium carbonate with 18-crown-6 ligand.

The deprotonation in b) with the aforementioned bases may preferably be performed in aprotic organic solvents or in liquid supercritical carbon dioxide or in liquid ammonia. Particular preference is given to ethers such as tetrahydrofuran, alkyl sulfoxides, such as DMSO, aromatic compounds such as toluene, aliphatic and cyclic alkanes such as n-hexane and cyclohexane, and alkylamides such as DMF.

The deprotonation may be effected in a temperature range of −80° C. to 100° C. This temperature range includes all values and subvalues therebetween, especially including −70° C. to 85° C., −60° C. to 70° C., −50° C. to 55° C., −40° C. to 40° C. and −30° C. to 25° C. A preferred range of −30° C. to 25° C., is advantageous for the reaction.

The hydrolysis in (b) may be effected preferably in aqueous solutions in the pH range of 1-14. This pH range includes all values and subvalues therebetween, especially including in the pH range of 1-6 or 8-13, and preferably in the range of pH 1-4 or pH 9-13.

The hydrolysis takes place at temperatures of −20° C. to 100° C. This temperature range includes all values and subvalues therebetween, including −10° C. to 65° C. and preferably, 0° C. to 30° C.

Thereafter, in step c), the acid-catalyzed solvolysis of the α,α-(dithio)carboxylic acid or derivatives thereof formed in b) is effected with release of thiols or salts thereof, and the product, depending in each case on the solvent used, may, for example, be the free α-keto acid and salts thereof, an α-keto ester, an α-keto amide, a ketal derivative of the α-keto acid or a ketal derivative of the α-keto ester (see also scheme).

Solvolysis is understood to mean the reaction of the α,α-(dithio)carboxylic acid with the solvent, for example, hydrolysis (with water).

The solvolysis may be effected generally under acid catalysis at temperatures of 20° C.-200° C. This temperature range includes all values and subvalues therebetween, including 30° C. to 180° C., 40° C. to 160° C. and preferably at 50-150° C.

Any acid catalyst suitable for solvolysis may be employed. Preferred catalysts include, for example, para-toluenesulfonic acid, $CF_3SO_3H$, mineral acids such as HCl or $H_2SO_4$, and strong organic acids which are non-nucleophilic.

The thiols of the formula $R^4SH$ formed during solvolysis may be removed from the reaction mixture by vacuum distillation or by distillation with introduction of an inert gas, wherein the thiol may be recycled and hence subsequently reused in the umpolung reaction. Other suitable separation processes may include, for example, phase separation, crystallization, complex formation or precipitation.

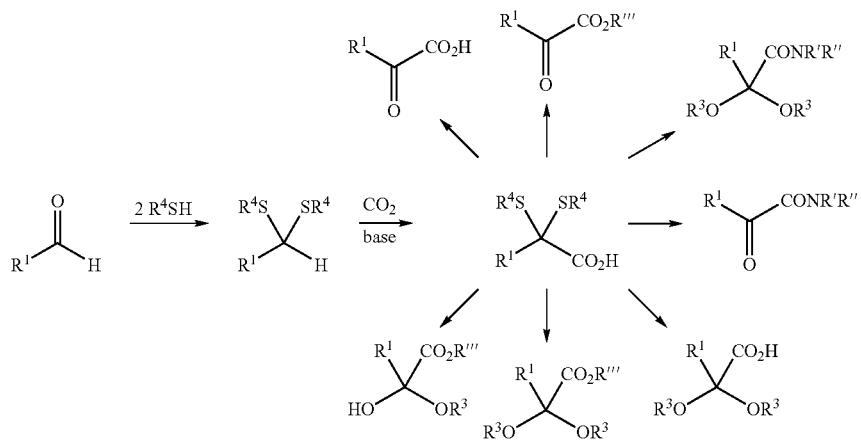

In a second embodiment, water is used as the solvent in the acid-catalyzed solvolysis in c), wherein the free α-keto acid of the formula (I), wherein $R^2$=OR''', R''' is a hydrogen atom and $R^1$ is as defined above, is formed.

In a third embodiment, in the acid-catalyzed solvolysis in c), an alcohol R'''OH, wherein R''' is a branched or straight-chain $C_1$-$C_8$-alkyl, $C_5$-$C_8$-cycloalkyl, allyl or benzyl group, and alkyl is optionally substituted is used as the solvent, in which case, the α-keto ester of the formula (I) wherein $R^2$=OR''', R''' is as defined hereinabove and $R^1$ as specified above, is formed.

In a fourth embodiment, in the acid-catalyzed solvolysis in c), a diol HO—$R^3$—OH, wherein $R^3$ is a branched or straight-chain, optionally substituted $C_2$-$C_8$-alkanediyl group, is used as the solvent, in which case, a cyclic ketal of the formula (II) is formed, wherein $R^2$=OR''', wherein R'''=H, $R^3$ is as defined hereinabove and $R^1$ as specified above.

In a fifth embodiment, in the acid-catalyzed solvolysis in c) a triol of the formula HOR(CHOH)R'''OH, wherein the $R^3$ and R''' radicals together are part of a branched or straight-chain, optionally substituted $C_3$-$C_8$-alkanetriyl group of the general formula —$R^3$(CH—)R''', is used as the solvent, in which case, a bicyclic ketal ester of the formula (II) is formed, wherein $R^2$=OR''', R''' and $R^3$ are each as defined hereinabove and $R^1$ is specified above.

In a sixth embodiment, in the acid-catalyzed solvolysis in c), an amine of the formula HNR'R'', wherein R' and R'' may be the same or different and are each a hydrogen atom or a branched or straight-chain $C_1$-$C_6$-alkyl group, wherein R' and R'' cannot both be a hydrogen atom, is used as the solvent. In this case, an amide of the formula (I), wherein $R^2$=NR'R'', and R' and R'' are each as defined hereinabove, is formed.

In the method for preparing α-keto acids and derivatives thereof according to the invention, the dithioacetal formed in a) also functions as a protecting group which, after the addition of carbon dioxide (b)), can be removed again in the presence of an acid by solvolysis (c)) under reduced pressure or by introducing an inert gas, for example nitrogen. It may be advantageous that the thiol released can then be recycled and reused.

In the case of α-ketomethionine, it may be advantageous to prepare the dithioacetal in a) either by reacting 3-(methylthio)propanal (=3-methylmercaptopropionaldehyde (MMP)) with methylthiol (MeSH) or directly from acrolein by the triple addition of methylthiol.

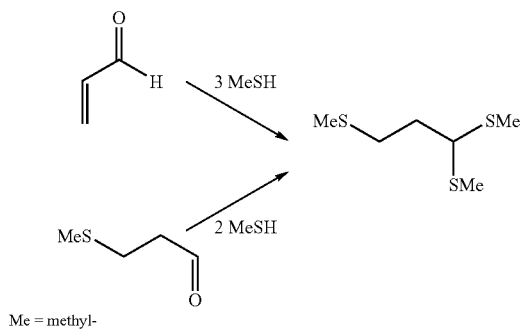

Me = methyl-

Compared to the previously cited conventional methods, the process according to the invention allows the preparation of α-keto acids or derivatives thereof in a higher yield, which constitutes a great economic advantage.

In addition, it is possible in the process according to the invention to continue to use the existing plants for preparing 3-(methylthio)propanal, i.e. the plants for preparing acrolein and methylthiol, in contrast to the process disclosed in WO 06-72711.

The process according to the invention is additionally environmentally friendly, since preference is given to using carbon dioxide as a C-1 unit, and hence contributes to climate protection (Kyoto Protocol).

In contrast to the process described in WO 06-72711 for preparing α-ketomethionine proceeding from butadiene, the process according to the invention has a high flexibility, since either the α-keto acid itself and also all derivatives, for example esters, ketals, etc. may be prepared directly.

The invention further provides the intermediate of the formula (IV),

wherein $R^1$ is a branched or straight-chain $C_1$-$C_{18}$-alkyl, $C_5$-$C_8$-cycloalkyl, vinyl, allyl, $C_6$-$C_{10}$-aryl-$C_1$-$C_4$-alkylene, preferably benzyl, or $C_4$-$C_9$-heteroaryl-$C_1$-$C_4$-alkylene group, preferably 4-imidazolylmethylene or 3-indolylmethylene, where $R^1$ is optionally substituted by —SH, —$SCH_3$, —COOH, —$CONH_2$, —CHO, guanidyl, —OH, —NR'R'' or —SS—$CH_2$—C(H)$NH_2$—$CO_2$H, where R' and R'' are each as defined below, $R^2$ is —OR''' or —NR'R'', in which R' and R'' may be the same or different and are each a hydrogen atom or a branched or straight-chain $C_1$-$C_6$-alkyl group, and R''' is a hydrogen atom, a branched or straight-chain $C_1$-$C_8$-alkyl, $C_5$-$C_8$-cycloalkyl, allyl or a benzyl group, where alkyl in R', R'' and/or R''' is optionally substituted, or R''' is an alkaline metal ion, alkaline earth metal ion or a mono- or divalent transition metal ion, and $R^4$ is the same or different and may be a branched or straight-chain, optionally substituted $C_1$-$C_6$-alkyl, $C_5$-$C_8$-cycloalkyl, allyl or benzyl group.

Preference is given to inventive intermediates of the formula (IV), in which $R^1$ is optionally substituted $C_1$-$C_4$-alkyl, especially $CH_3SCH_2CH_2$.

The invention further provides for the use of a thiol of the formula $R^4$—S—H, where $R^4$ is a branched or straight-chain, optionally substituted $C_1$-$C_6$-alkyl, $C_5$-$C_8$-cycloalkyl, allyl or benzyl group for umpolung of aliphatic and/or aromatic aldehydes.

Having generally described this invention, a further understanding can be obtained by reference to certain specific examples which are provided herein for purposes of illustration only, and are not intended to be limiting unless otherwise specified.

EXAMPLES

Example 1

Preparation of 1,1,3-tris(methylthio)propane (2) from 3-(methylthio)propanal (1)

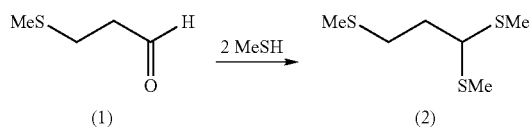

Me = methyl 3-(methylthio)propanal (1) (1.44 mol, 150 g) was saturated at 0° C. with HCl (g) and then added dropwise directly to MeSH (6.25 mol, 300 g) at 0° C. over a period of 30 minutes. The reaction mixture was heated to 20° C. and stirred at 20° C. for 24 h. After the excess MeSH had been removed under reduced pressure, GC analysis showed the following product distribution: 91% thioacetal (2) and 8% 3-(methylthio)propanal (1). For further purification, this mixture was dissolved in diethyl ether and washed with a 30% aqueous sodium pyrosulfite ($Na_2SO_2O_5$) solution. After phase separation, the organic phase was dried over $MgSO_4$. After the solvent had been removed, the thioacetal (2) was obtained as a pale-yellow colored oil (168 g, yield=64%, GC purity=98%).

$^1$H NMR of 1,1,3-tris(methylthio)propane (2) (500 MHz, $CDCl_3$): δ=2.01-2.05 (m, 2H, $CH_2$), 2.11 (s, 9H, 3×$SCH_3$), 2.71 (t, $^3J$=7.3 Hz, 2H, $CH_2$), 3.83 (t, $^3J$=7.3 Hz, 1H, CH)

$^{13}$C NMR of 1,1,3-tris(methylthio)propane (2) (125.8 MHz, $CDCl_3$: δ=12.6 (2×$SCH_3$), 15.5 ($SCH_3$), 32.0 ($CH_2$), 33.9 ($CH_2$), 53.0 ($C(SCH_3)_2$)

Example 2

Preparation of 1,1,3-tris(methylthio)propane (2) from acrolein (3)

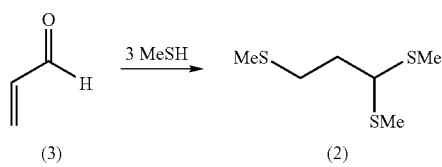

Acrolein (3) (89 mmol, 5.0 g) was added dropwise at −78° C. with stirring to MeSH (358 mmol, 17.2 g), which had been saturated with HCl gas at 0° C., over a period of 15 minutes. This mixture was heated slowly to 20° C. and then stirred further at 20° C. for 24 h. After removal of the excess MeSH under reduced pressure, this mixture was dissolved in diethyl ether and washed with a 30% aqueous sodium pyrosulfite solution. After phase separation, the organic phase was dried over $MgSO_4$. After distillation (88° C. at 1.2 mbar), the pure thioacetal (2) was obtained as a pale-yellow colored oil (11.4 g, yield=70%, GC purity=98%). The NMR characterization gave the same data as in Example 1.

Example 3

Preparation of 2,2,4-tris(methylthio)butanoic acid (4) by umpolung reaction of 1,1,3-tris(methylthio)propane (2) with dry ice ($CO_2$)

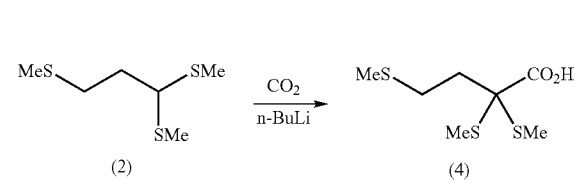

In a three-neck flask under a protective gas atmosphere, 1,1,3-tris(methylthio)propane (2) (3.65 g, 20 mmol) was dissolved in 50 ml of abs. THF. Subsequently, at −20° C., a butyllithium solution in n-hexane (14 ml, 1.6 M) was slowly added dropwise with stirring. In the course of this, the solution turned bright yellow. After stirring had been continued at this temperature for a further 2 h, anhydrous dry ice ($CO_2$, 10 g) which had been washed beforehand in abs. THF was added in portions at −70° C. The reaction solution was thawed slowly to 20° C. and a 10% aqueous KOH solution (80 ml) was added. After phase separation, the organic phase was washed with 10% aqueous KOH solution (2×50 ml). The combined KOH phases were washed with diethyl ether (3×30 ml) and then adjusted cautiously to pH 1 with conc. HCl while cooling. The product was extracted with diethyl ether (3×50 ml). The combined ether phases were subsequently dried over $Na_2SO_4$ and, after filtration, concentrated on a rotary evaporator. 2,2,4-tris(methylthio)butanoic acid (4) was obtained as a yellowish oil (4.3 g, yield=95%), which crystallized slowly when left to stand.

$^1$H NMR of 2,2,4-tris(methylthio)butanoic acid (4) (500 MHz, $CDCl_3$): δ=2.12 (s, 6H, 2×$SCH_3$), 2.14 (s, 3H, $SCH_3$), 2.22-2.26 (m, 2H, $CH_2$), 2.67-2.70 (m, 2H, $CH_2$)

$^{13}$C NMR of 2,2,4-tris(methylthio)butanoic acid (4) (125.8 MHz, $CDCl_3$): δ=12.5 (2×$SCH_3$), 15.6 (C-5), 29.7 (C-3), 34.6 (C-4), 63.5 (C-2), 175.3 ($CO_2H$)

Example 4

Preparation of calcium 2,2,4-tris(methylthio)butanoate (5) from the corresponding α,α-(dialkylthio)carboxylic acids (4)

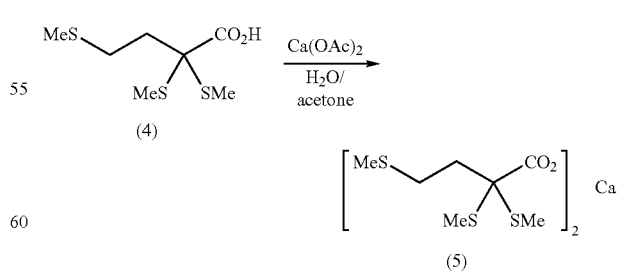

16.6 g of 2,2,4-tris(methylthio)butanoic acid (4) (73.3 mmol) were dissolved in a mixture of 140 ml of $H_2O$ and 35 ml of acetone. Subsequently, a solution of 6.2 g of calcium acetate (93%) and 22 ml of $H_2O$ was slowly added dropwise at 20° C. with vigorous stirring. After a short time a white solid precipitated out which was filtered off after 30 minutes. The resulting white solid was washed twice with 200 ml of H₂O each time, then with 200 ml of acetone and 200 ml of diethyl ether, and dried in a drying cabinet. A total of 17.7 g of calcium 2,2,4-tris(methylthio)butanoate (5) (M=490.8 g/mol, yield=98%) were isolated.

¹H NMR of calcium 2,2,4-tris(methylthio)butanoate (5) (500 MHz, DMSO-D₆): δ=1.93 (s, 6H, 2 SCH₃), 1.95-1.99 (m, 2H, CH₂), 2.05 (s, 3H, SCH₃), 2.52-2.55 (m, 2H, CH₂)

Example 5

Preparation of 2,2,4-tris(methylthio)butanoic acid (4) by umpolung reaction of 1,1,3-tris(methylthio)propane (2) with gaseous CO₂

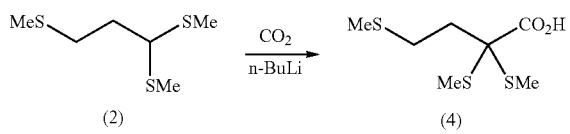

In a three-neck flask under a protective gas atmosphere, 1,1,3-tris(methylthio)propane (2) (3.65 g, 20 mmol) was dissolved in 50 ml of abs. THF. Subsequently, at −20° C., a butyllithium solution in n-hexane (14 ml, 1.6 M) was slowly added dropwise with stirring. In the course of this, the solution turned bright yellow. After stirring had been continued at this temperature for 2 h, gaseous dry CO₂ was passed through via a frit at −70° C. over a period of 30 minutes. The reaction solution was thawed slowly until a temperature of 20° C. was attained, at which a 10% aqueous KOH solution (80 ml) was added. After phase separation, the organic phase was washed with 10% aqueous KOH solution (2×50 ml). The combined KOH phases were washed with diethyl ether (3×30 ml) and then adjusted cautiously to pH 1 with conc. HCl while cooling. The product was extracted with diethyl ether (3×50 ml). The combined ether phases were subsequently dried over Na₂SO₄ and, after filtration, concentrated on a rotary evaporator. 2,2,4-tris(methylthio)butanoic acid (4) was obtained as a yellowish oil (4.1 g, yield=90%), which crystallized slowly when left to stand. The NMR characterization gave the same data as in Example 3.

Example 6

Preparation of ketomethionine isopropyl ester (6) by removal of the thiol from 2,2,4-tris(methylthio)-butanoic acid (4) in the presence of isopropanol

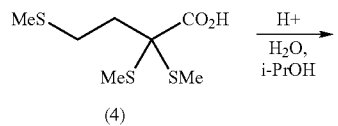

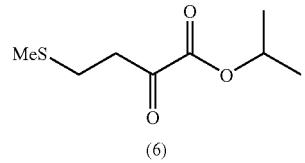

0.1 mol of 2,2,4-tris(methylthio)butanoic acid (4) (22.6 g) was dissolved in a mixture of 200 ml of toluene and 200 ml of isopropanol. Subsequently, 2.0 eq of H₂O (3.6 ml) and one spatula-tip of p-toluenesulfonic acid monohydrate were added. The overall mixture was then heated to boiling temperature and stirred under reflux for 3 h. After cooling, 150 ml of water were added and the mixture was extracted three times with 100 ml each time of diethyl ether. The combined ether phases were subsequently washed to neutrality with a dilute sodium hydrogencarbonate solution, and dried over magnesium sulfate. After filtration, all of the solvent was drawn off with a rotary evaporator. Ketomethionine isopropyl ester (6) (14.5 g, yield=76%) was obtained as a pale yellowish oil.

¹H NMR of ketomethionine isopropyl ester (6) (500 MHz, CDCl₃): δ=1.35 (d, ³J=6.3 Hz, 6H, 2 CH₃), 2.14 (s, 3H, SCH₃), 2.79 (t, ³J=7.2 Hz, 2H, CH₂), 3.15 (t, ³J=7.2 Hz, 2H, CH₂), 5.15 (quint, ³J=6.3 Hz, 1H, CH)

Elemental analysis for C₈H₁₄O₃S (6) (M=190.26 g/mol): C 50.50; H 7.43; S 16.85 found: C 50.66; H 7.57; S 16.52

Example 7

Direct preparation of ketomethionine ethylene glycol ketal (7) by removing the thiol from 2,2,4-tris(methylthio)butanoic acid (4) in the presence of ethylene glycol

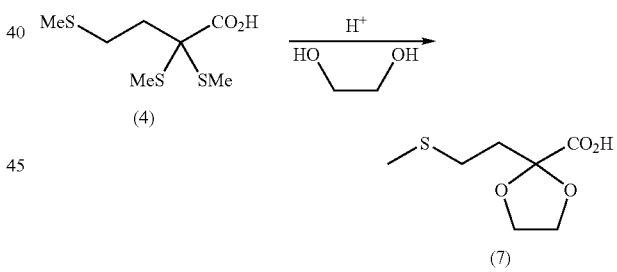

0.1 mol of 2,2,4-tris(methylthio)butanoic acid (4) (22.6 g) was dissolved in 200 ml of ethylene glycol (1,2-ethanediol). Subsequently, 1.1 eq of H₂O (1.8 ml) and a spatula-tip of p-toluenesulfonic acid monohydrate were added. The overall mixture was then heated to 50° C. and a constant nitrogen stream was passed through the solution via a frit. After 4 h, the reaction mixture was added to 300 ml of water and extracted three times with 100 ml each time of diethyl ether. The combined ether phases were dried over MgSO₄. After filtration, the ether was drawn off with a rotary evaporator. Subsequently, 100 ml of methanol and 100 ml of 2 M NaOH solution were added to the ester, protected as the ketal, and the mixture was stirred at 20° C. for 2 h. Thereafter, the solution was acidified to pH=1 with conc. HCl and extracted three times with 100 ml each time of diethyl ether. The combined ether phases were subsequently dried over MgSO₄. After filtration, the ether was drawn off and the crude product was crystallized from a mixture of methylene chloride and n-hexane. 13.0 g of a white crystalline solid (7) were obtained. (Yield=68%, M=192.23 g/mol, melting point: 74° C. (crystallized from methylene chloride/n-hexane)).

$^1$H NMR of 2-(2-(methylthio)ethyl)-1,3-dioxolane-2-carboxylic acid (7) (500 MHz, CDCl$_3$): δ=2.11 (s, 3H, SCH$_3$), 2.24-2.28 (m, 2H, CH$_2$), 2.58-2.61 (m, 2H, CH$_2$), 4.07-4.14 (m, 4H, OCH$_2$CH$_2$O)

$^{13}$C NMR of 2-(2-(methylthio)ethyl)-1,3-dioxolane-2-carboxylic acid (7) (125.8 MHz, CDCl$_3$): δ=15.5 (SCH$_3$), 27.1 (CH$_2$), 34.9 (CH$_2$), 66.1 (2 OCH$_2$), 105.9 (C), 174.1 (COO)

Elemental analysis for C$_7$H$_{12}$O$_4$S (7) (M=192.24 g/mol): C 43.74; H 6.29; S 16.68 found: C 43.80; H 6.25; S 16.61

Example 8

Direct preparation of ketomethionine ketal ester (8a)/(8b) by removal of the thiol from the α,α-(dialkylthio)carboxylic acid (4) in the presence of glycerol

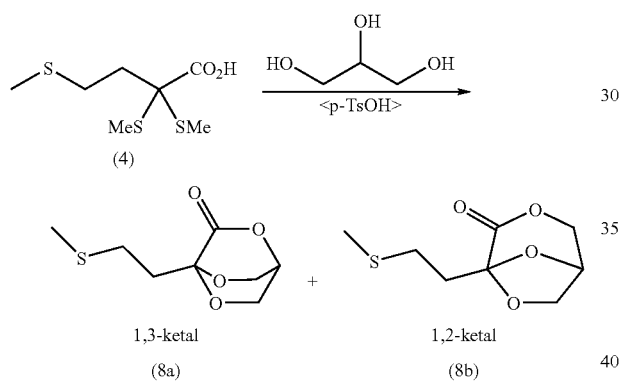

0.1 mol of 2,2,4-tris(methylthio)butanoic acid (4) (22.6 g) was dissolved in 100 ml of glycerol (1,2,3-propanetriol). Subsequently, 1.1 eq of H$_2$O (1.8 ml) and a spatula-tip of p-toluenesulfonic acid monohydrate were added. The overall mixture was then heated to 70° C. and a vacuum of 750 mbar was applied. After 5.5 h, the reaction mixture was added to 300 ml of water and extracted three times with 100 ml each time of diethyl ether. The combined ether phases were dried over MgSO$_4$. After filtration, the ether was removed on a rotary evaporator and the oily crude product ((8a):(8b) ratio=70:30) was crystallized from a mixture of methylene chloride/n-hexane. The main product (8a) crystallized out in the form of colorless needles (9.2 g, yield=45%, M=204.25 g/mol, melting point=39.5° C. (recrystallized from methylene chloride/n-hexane)).

$^1$H NMR of 4-(2-(methylthio)ethyl)-2,5,8-trioxabicyclo[2.2.2]octan-3-one (8a) (500 MHz, CDCl$_3$): δ=2.13 (s, 3H, SCH$_3$), 2.17-2.20 (m, 2H, CH$_2$), 2.65-2.68 (m, 2H, CH$_2$), 4.12-4.13 (m, 4H, 2 CH$_2$), 4.76 (s, 1H, CH)

$^{13}$C NMR of 4-(2-(methylthio)ethyl)-2,5,8-trioxabicyclo[2.2.2]octan-3-one (8a) (125.8 MHz, CDCl$_3$): δ=15.4 (SCH$_3$), 26.9 (CH$_2$), 33.2 (CH$_2$), 66.5 (2 OCH$_2$), 70.9 (CH), 92.9 (C), 166.2 (COO)

Elemental analysis for C$_8$H$_{12}$O$_4$S (8a) (M=204.25 g/mol): C 47.04; H 5.92; S 15.70 found: C 47.21; H 5.93; S 15.69

Example 9

Preparation of 1,1-bis(methylthio)butane (10)

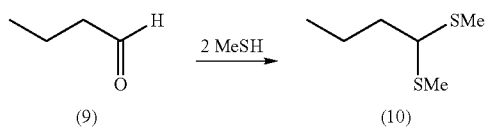

10.0 g of butanal (9) (139 mmol) were saturated with HCl (g) at 0° C. and then added dropwise directly to MeSH (624 mmol, 30.0 g) at 0° C. over a period of 25 minutes. The reaction mixture was heated to 20° C. and stirred at 20° C. for 17 h. For further purification, this mixture was dissolved in diethyl ether and washed with a 30% aqueous sodium pyrosulfite solution. After phase separation, the organic phase was dried over Na$_2$SO$_4$. After the solvent had been removed, the thioacetal (10) was obtained as a clear colorless oil (17.3 g, yield=83%; GC purity 98%). The NMR data agree with those from the literature.

Example 10

Preparation of 1,1-bis(methylthio)pentanoic acid (11) by umpolung reaction of 1,1-bis(methylthio)butane (10) with dry ice (CO$_2$)

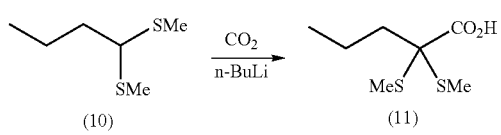

10 mmol of 1,1-bis(methylthio)butane (10) (1.26 g) were initially charged in 25 ml of dry THF under a nitrogen atmosphere and cooled to −20° C. Subsequently, 11 mmol of 1.6 M n-BuLi solution in n-hexane (7.0 ml) were added dropwise at −20° C. over a period of 5 minutes, and the mixture was stirred for 2 h. The clear, pale yellow reaction solution was added dropwise to 15 g of dry ice at −78° C. and stirred for 36 h, in the course of which the temperature rose to 20° C. overnight. Subsequently, the reaction mixture was admixed with 40 ml of 10% KOH solution and the phases were separated. The organic phase was washed twice with 25 ml each time of 10% KOH solution, and the combined KOH phases were washed three times with 25 ml each time of methyl tert-butyl ether (MTBE). The KOH phase was then acidified (pH 1) with conc. HCl (aq) and extracted four times with 25 ml each time of MTBE. The combined organic phases were dried over MgSO$_4$ and concentrated with a rotary evaporator. The 2,2-(dimethylthio)pentanoic acid (11) was obtained as a white solid (1.0 g, yield=51.5%, melting point=85° C. (recrystallized from a mixture of chloroform, methanol and acetic acid)).

$^{13}$H NMR of 2,2-(dimethylthio)pentanoic acid (11) (500 MHz, CDCl$_3$): δ=0.96 (t, $^3J$=7.4 Hz, 3H, C$^5$H$_3$), 1.50-1.60 (m, 2H, C$^4$H$_2$), 1.88-1.94 (m, 2H, C$^3$H$_2$), 2.10 (s, 6H, 2×SCH$_3$), 11.5 (bs, 1H, C$^1$OOH)

$^{13}$C NMR of 2,2-(dimethylthio)pentanoic acid (11) (125.8 MHz, CDCl$_3$): δ=12.5 (2×SCH$_3$), 14.0 (C-5), 15.1 (C-4), 36.9 (C-3), 64.6 (C-2), 176.3 (C-1)

Example 11

Preparation of ethyl 2-oxovalerate (12) by removing the thiol from 2,2-(dimethylthio)pentanoic acid (11) in the presence of water and ethanol

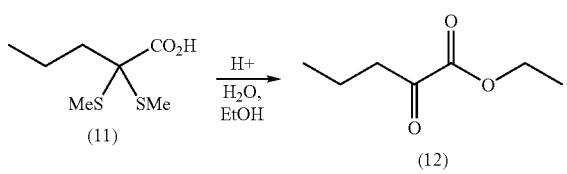

0.1 mol of 2,2-(dimethylthio)pentanoic acid (11) (19.4 g) was dissolved in 150 ml of toluene and admixed with 2.0 eq of H$_2$O (3.6 ml) and a spatula-tip of p-toluenesulfonic acid monohydrate. Subsequently, the mixture was heated to boiling point and a nitrogen stream was passed through the solution via a frit. After 3 h under reflux, the reaction mixture was cooled to 80° C. and admixed with 200 ml of ethanol and a further spatula-tip of p-toluenesulfonic acid monohydrate. After a further 3 h under reflux, the mixture was cooled to 20° C., 200 ml of water were added and the mixture was extracted three times with 100 ml each time of diethyl ether. The combined ether phases were subsequently washed to neutrality with a dilute sodium hydrogencarbonate solution and dried over magnesium sulfate. After filtration, all of the solvent was drawn off with a rotary evaporator. The ethyl 2-oxovalerate (12) (10.2 g, yield=71%) was obtained as a pale yellowish oil.

$^1$H NMR of ethyl 2-oxovalerate (12) (500 MHz, CDCl$_3$): δ=0.97 (t, $^3$J=7.3 Hz, 3H, C$^5$H$_3$), 1.37 (t, $^3$J=7.3 Hz, 3H, OCH$_2$CH$_3$), 1.67 (sext, $^3$J=7.3 Hz, 2H, C$^4$H$_2$), 2.81 (t, $^3$J=7.3 Hz, 2H, C$^3$H$_3$), 4.32 (q, $^3$J=7.3 Hz, 2H, OCH$_2$CH$_3$)

$^{13}$C NMR of ethyl 2-oxovalerate (12) (125.8 MHz, CDCl$_3$): δ=13.5 (OCH$_2$CH$_3$), 14.0 (C-5), 16.6 (C-4), 41.2 (C-3), 62.3 (OCH$_2$CH$_3$), 161.4 (C-1), 194.7 (C-2)

Example 12

Preparation of 2-oxovaleric acid (13) by removing the thiol from 2,2-(dimethylthio)pentanoic acid (11) in the presence of water

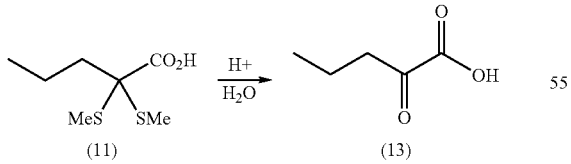

10.0 mmol of 2,2-(dimethylthio)pentanoic acid (11) (1.94 g) were suspended in 30 ml of fuming hydrochloric acid (37%) and admixed with a spatula-tip of p-toluenesulfonic acid monohydrate. Subsequently, the mixture was heated to boiling temperature and stirred for 5 h. A vacuum of 750 mbar was applied. After the reaction, the mixture was diluted with 100 ml of water and extracted three times with 80 ml each time of diethyl ether. The combined organic phases were washed three times with 100 ml each time of sodium hydrogencarbonate solution. The combined aqueous phases were subsequently acidified to pH=1 with concentrated hydrochloric acid and extracted three times with 100 ml each time of diethyl ether. The combined ether phases were dried over MgSO$_4$ and filtered, and the filtrate was concentrated to dryness under reduced pressure at room temperature. 2-oxovaleric acid (13) was obtained as a colorless oil (0.72 g, yield=62%).

$^1$H NMR of 2-oxovaleric acid (13) (500 MHz, DMSO-D6): δ=0.88 (t, $^3$J=7.4 Hz, 3H, C$^5$H$_3$), 1.53 (sext, $^3$J=7.4 Hz, 2H, C$^4$H$_2$), 1.96 (t, $^3$J=7.4 Hz, 2H, C$^3$H$_3$), 13.5 (bs, 1H, COOH)

$^{13}$C NMR of 2-oxovaleric acid (13) (125.8 MHz, DMSO-D6): δ=13.64 (C-5), 16.37 (C-4), 40.56 (C-3), 163.28 (C-1), 196.93 (C-2)

Numerous modifications and variations on the present invention are possible in light of the above teachings. It is therefore to be understood that within the scope of the appended claims, the invention may be practiced otherwise than as specifically described herein.

The invention claimed is:
1. A method, comprising:
a) reacting an aldehyde represented by R$^1$CHO with at least two thiols represented by R$^4$—S—H, to give a dithioacetal;
b) reacting the dithioacetal with a carbonyl-containing electrophile in the presence of a strong base that comprises at least one member selected from the group consisting of n-butyllithium, tert-butyllithium, sodium amide, sodium hydride, potassium hydroxide, and potassium carbonate and hydrolyzing in a solvent represented by R$^5$OH to give an α,α-(dithio)carboxylic acid or a derivative thereof represented by formula (III):

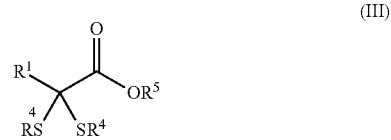

(III)

c) converting the α,α-(dithio)carboxylic acid or derivative thereof represented by formula (III) by acid-catalyzed solvolysis in the presence of at least one molar equivalent of water with release of thiols of the formula R$^4$SH to give at least one of an α-keto acid represented by formula (I) and a compound represented by formula (II)

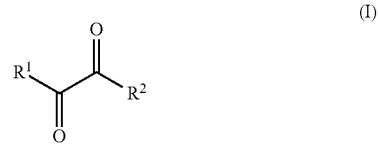

(I)

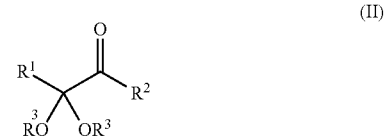

(II)

wherein
- $R^1$ is an optionally substituted, branched or straight-chain $C_1$-$C_{18}$-alkyl, $C_5$-$C_8$-cycloalkyl, vinyl, allyl, $C_6$-$C_{10}$-aryl-$C_1$-$C_4$-alkylene or $C_4$-$C_9$-heteroaryl-$C_1$-$C_4$-alkylene group,
- $R^2$ is —OR''' or —NR'R'', in which R' and R'' are the same or different and are each a hydrogen atom or a branched or straight-chain $C_1$-$C_6$-alkyl group, and R''' is a hydrogen atom, a branched or straight-chain $C_1$-$C_8$-alkyl, $C_5$-$C_8$-cycloalkyl, allyl or a benzyl group, where the alkyl in R', R'' and R''' is optionally substituted, or R''' is an alkaline metal ion, alkaline earth metal ion or a mono- or divalent transition metal ion,
- $R^3$ is the same or different and is a hydrogen atom, a branched or straight-chain $C_1$-$C_8$-alkyl, allyl or a benzyl group, where alkyl and/or benzyl is optionally substituted, or the two $R^3$ radicals together are $C_2$-$C_8$-alkanediyl and together form a ring, or the two $R^3$ and R''' radicals together are part of a $C_3$-$C_8$-alkanetriyl group of the general formula —$R^3$(CH—)R''' and together form a bicyclic group,
- $R^4$ is a branched or straight-chain, optionally substituted $C_1$-$C_6$-alkyl, $C_5$-$C_8$-cycloalkyl, allyl or benzyl group, and
- $R^5$ is a hydrogen atom or a branched or straight-chain $C_1$-$C_6$-alkyl group, wherein the acid-catalyzed solvolysis in c) is carried out in the presence of a solvent that comprises at least one of:
  - a diol represented by HO—$R^7$—OH, wherein $R^7$ is a branched or straight-chain, optionally substituted $C_2$-$C_8$-alkanediyl group;
  - a triol represented by HOR$^8$(CHOH)R$^9$OH, wherein the $R^8$ and $R^9$ radicals together are part of a branched or straight-chain, optionally substituted $C_3$-$C_8$-alkanetriyl group of the general formula —$R^8$(CH—)$R^9$; and
  - an amine represented by HNR$^{10}$R$^{11}$ wherein R$^{10}$ and R$^{11}$ may be the same or different and are each a hydrogen atom or a branched or straight-chain $C_1$-$C_6$-alkyl group, with the proviso that R$^{10}$ and R$^{11}$ cannot both be a hydrogen atom.

2. The method according to claim 1, wherein said b) reacting is carried out in the presence of one solvent selected from the group consisting of an aprotic organic solvent, liquid supercritical carbon dioxide and liquid ammonia.

3. The method according to claim 1, wherein said b) reacting is carried out at a temperature of from −80° C. to 100° C.

4. The method according to claim 1, further comprising removing the thiol represented by R$^4$SH released in the acid-catalyzed solvolysis, recycling and reusing the thiol the reaction of the aldehyde to give the corresponding dithioacetal.

5. The method according to claim 4, wherein
the thiol represented by R$^4$SH is a $C_1$-$C_6$-alkylthiol and
the removal of the thiol comprises removal by applying a vacuum to or by passing inert gas through the solvolysis mixture.

6. The method according to claim 4, wherein the thiol represented by R$^4$SH is methylthiol.

7. The method according to claim 1, wherein the acid-catalyzed solvolysis is carried out in the presence of a solvent comprising water.

8. The method according to claim 1, wherein the acid-catalyzed solvolysis is carried out in the presence of a solvent comprising an alcohol represented by R$^6$OH,
wherein R$^6$ is a branched or straight-chain optionally substituted $C_1$-$C_8$-alkyl, $C_5$-$C_8$-cycloalkyl, allyl or a benzyl group.

9. The method according to claim 1, wherein the acid-catalyzed solvolysis is carried out in the presence of a solvent comprising a diol represented by HO—R$^7$—OH,
wherein R$^7$ is a branched or straight-chain, optionally substituted $C_2$-$C_8$-alkanediyl group.

10. The method according to claim 1, wherein the acid-catalyzed solvolysis is carried out in the presence of a solvent comprising a triol represented by HOR$^8$(CHOH)R$^9$OH,
wherein the R$^8$ and R$^9$ radicals together are part of a branched or straight-chain, optionally substituted $C_3$-$C_8$-alkanetriyl group of the general formula —R$^8$(CH—)R$^9$.

11. The method according to claim 1, wherein the acid-catalyzed solvolysis is carried out in the presence of a solvent comprising an amine represented by HNR$^{10}$R$^{11}$
wherein R$^{10}$ and R$^{11}$ may be the same or different and are each a hydrogen atom or a branched or straight-chain $C_1$-$C_6$-alkyl group,
with the proviso that R$^{10}$ and R$^{11}$ cannot both be a hydrogen atom.

12. The method according to claim 1, wherein R$^1$ in the aldehyde represented by R$^1$CHO is vinyl or CH$_3$SCH$_2$CH$_2$—.

13. The method according to claim 1, wherein R$^1$ is CH$_3$SCH$_2$CH$_2$—, and R$^4$ is methyl.

14. The method according to claim 1, wherein
the aldehyde represented by R$^1$CHO is acrolein,
the α-keto acid of the general formula (I) is α-ketomethionine and/or derivatives thereof, and
the reacting the aldehyde further comprises addition of methylthiol to the carbon-carbon double bond of acrolein.

15. A method for umpolung of an aliphatic or aromatic aldehyde, comprising:
reacting an aldehyde represented by R$^1$CHO with a thiol represented by R$^4$SH,
wherein R$^1$ is CH$_3$SCH$_2$CH$_2$—, and R$^4$ is methyl.

16. The method according to claim 1, wherein the carbonyl-containing electrophile is one carbonyl-containing electrophile selected from the group consisting of carbon dioxide, phosgene, a chloroformate ester, an orthoformic ester and a dialkylcarbonate.

17. The method according to claim 16, wherein the carbonyl-containing electrophile is carbon dioxide.

18. The method according to claim 1, which results in the α-keto acid represented by formula (I)

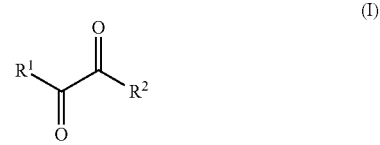

19. The method according to claim 1, which results in the α-keto acid derivative represented by formula (II)

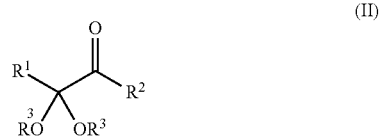

20. The method according to claim 1, wherein $R^1$ is a branched or straight-chain $C_1$-$C_{18}$-alkyl, $C_5$-$C_8$-cycloalkyl, vinyl, allyl, $C_6$-$C_{10}$-aryl-$C_1$-$C_4$-alkylene or $C_4$-$C_9$-heteroaryl-$C_1$-$C_4$-alkylene group, where $R^1$ is optionally substituted with at least one substitute selected from the group consisting of —SH, —SCH$_3$, —COOH, —CONH$_2$, —CHO, guanidyl, —OH, —NR'R" and —SS—CH$_2$—C(H)NH$_2$—CO$_2$H, where R' and R" of —NR'R" are the same or different and are each a hydrogen atom or a branched or straight-chain $C_1$-$C_6$-alkyl group.

* * * * *